(12) United States Patent
Günther et al.

(10) Patent No.: US 6,598,507 B1
(45) Date of Patent: Jul. 29, 2003

(54) MICROTOME

(75) Inventors: Bernd Günther, Neidenstein (DE); Andreas Laudat, Meckesheim (DE); Jürgen Vierling, Eppelheim (DE); Roland Walter, Altlussheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 0 days.

(21) Appl. No.: 09/524,543

(22) Filed: Mar. 13, 2000

(30) Foreign Application Priority Data

Mar. 12, 1999  (DE) .......................... 199 11 163

(51) Int. Cl.[7] .................................. B26D 5/20
(52) U.S. Cl. ...................... 83/76.9; 83/703; 83/915.3
(58) Field of Search ........................ 83/76.9, 915.5, 83/703, 403.1, 733

(56) References Cited

U.S. PATENT DOCUMENTS

| | | | | |
|---|---|---|---|---|
| 3,771,405 A | * | 11/1973 | Blum ........................... 83/714 |
| 4,930,882 A | * | 6/1990 | Koch et al. .................. 350/530 |
| 5,065,657 A | * | 11/1991 | Pfeifer ....................... 83/915.5 |
| 5,070,935 A | * | 12/1991 | Sitte et al. .................. 83/915.5 |
| 5,181,443 A | * | 1/1993 | Sitte et al. ..................... 83/72 |
| 5,226,335 A | * | 7/1993 | Sitte et al. ................... 83/76.7 |
| 5,671,648 A | | 9/1997 | Dern ......................... 83/411.1 |
| 5,699,688 A | * | 12/1997 | Allred ........................ 72/20.5 |
| 5,761,977 A | * | 6/1998 | Jakobi et al. ................. 83/13 |
| 5,881,626 A | * | 3/1999 | Kiene et al. ................. 83/707 |
| 5,960,690 A | * | 10/1999 | Romi .......................... 82/133 |

FOREIGN PATENT DOCUMENTS

| | | |
|---|---|---|
| DE | 31 27 266 | 1/1983 |
| DE | 88 09 096.5 | 7/1988 |
| WO | WO 91/15746 | 10/1991 |
| WO | WO 98/04898 | 2/1998 |

* cited by examiner

Primary Examiner—Kenneth E. Peterson
Assistant Examiner—Omar Flaves-Sánchez
(74) Attorney, Agent, or Firm—Foley & Lardner

(57) ABSTRACT

A microtome for producing thin sections, in which the cutting operation is performed by way of a relative movement between a cutting knife and an object. A drive system (14) having a drive motor (17), a control circuit (15), and a handwheel (8) is provided to generate the relative movement. The handwheel (8) is connected to an encoder (16) that delivers corresponding signals to the control circuit (15) upon rotation of the handwheel (8). The drive motor (17) is then activated accordingly by way of said control circuit (15). In the absence of encoder signals, the drive system (14) is locked.

24 Claims, 1 Drawing Sheet

MICROTOME

BACKGROUND OF THE INVENTION

1. Field of the Invention

The present invention concerns a microtome for producing thin sections, in which the cutting operation is performed by way of a relative movement between a cutting knife and an object. A drive system having a drive motor, a control circuit, and a handwheel is provided to generate the relative movement.

Microtomes are increasingly being automated in order to minimize the continuous stress on the operator and at the same time to ensure simplified handling. In addition, the throughput of specimens to be sectioned is increased with a correspondingly automated microtome. In automated microtomes, for example, developments have included not only automatically feeding the object onto the cutting knife, but additionally equipping the drive system with a motor that generates a relative movement between the object and the cutting knife. A microtome of this kind is depicted and described, for example, in WO 98 04 898 A1.

With automatically operating microtomes it has also been found, however, that in certain situations it is impossible to dispense with manual intervention by the operator. The motorized drive system must be operated as slowly as possible, for example, after an object has been changed in order to align the object, and when sectioning of the object first begins. With automated microtomes, however, only control panels with corresponding switches are provided to control operation. Sensitive, manually controlled operation can be achieved only to a limited extent with switches.

During alignment of the object, it is also necessary for the object and the cutting knife to be fed toward one another, then a visual check is made, and then a slight reverse motion is performed. These degrees of freedom are necessary for alignment. Once achieved, the alignment is then checked visually by feeding again, and is again corrected if necessary. To ensure perfect cuts, this procedure must be performed with the greatest of care. With simple rocker switches, a motor-driven microtome cannot be controlled with sufficient accuracy for such a procedure.

The motorized drive systems also suffer from the disadvantage that, in zero-current standby mode, the drive system can be moved manually. This is dangerous, in particular when a knife or preparation is being changed, since the operator's hand may slip against the components, and can be pulled against the knife edge by the moving drive.

2. Description of the Related Art

U.S. Pat. No. 5,671,648 discloses a microtome for producing thin sections for microscopy. This microtome has a stationary cutting knife and an object holder, arranged on a rotatably mounted disk, with the object that is to be sectioned. The height of the disk can be changed in order to feed the object onto the cutting knife. The feed device is equipped with a motor and a control circuit. A drive-train linkage with a handwheel is provided as the drive device for the rotatable disk. In addition, a drive motor that is connected to the drive train can be arranged in the microtome. This document does not stipulate whether the drive motor replaces the handwheel, or how the drive motor is activated.

DE 88 09 096 U1 discloses a microtome having retractable operating knobs that are connected to a drive train for manual adjustment of the parameters that can be selected on the microtome, for example, section thickness, knife angle, etc. The drive train in this case is connected to an electronic generator that converts the rotary motion at the operating knobs into corresponding electrical signals. The drive motors for setting the parameters are controlled by way of a control device. No motor drive for preparation sectioning is provided in this microtome; all that is depicted is a conventional drive-train drive system using a handwheel.

SUMMARY OF THE INVENTION

It is one object of the present invention to provide an improved microtome having a motorized drive system that is capable as well of sensitive, manually controlled operation, and that assures a high level of operating safety, even in standby mode.

In accomplishing the foregoing objects, there has been provided in accordance with the present invention a microtome for producing thin sections from an object, comprising: a housing; a cutting blade; and a drive system for producing relative movement between the cutting knife and the object. The drive system has a drive motor, a control circuit, and a handwheel, wherein the handwheel is connected to an encoder for delivering corresponding signals to the control circuit upon rotation of the handwheel, and the control circuit is configured to activate the drive motor in accordance with the signals and to lock the drive system in the absence of encoder signals.

Further objects, features and advantages of the present invention will become apparent from the detailed description of preferred embodiments that follows, when considered together with the accompanying figures of drawing.

DETAILED DESCRIPTION OF PREFERRED EMBODIMENTS

Figure 1:
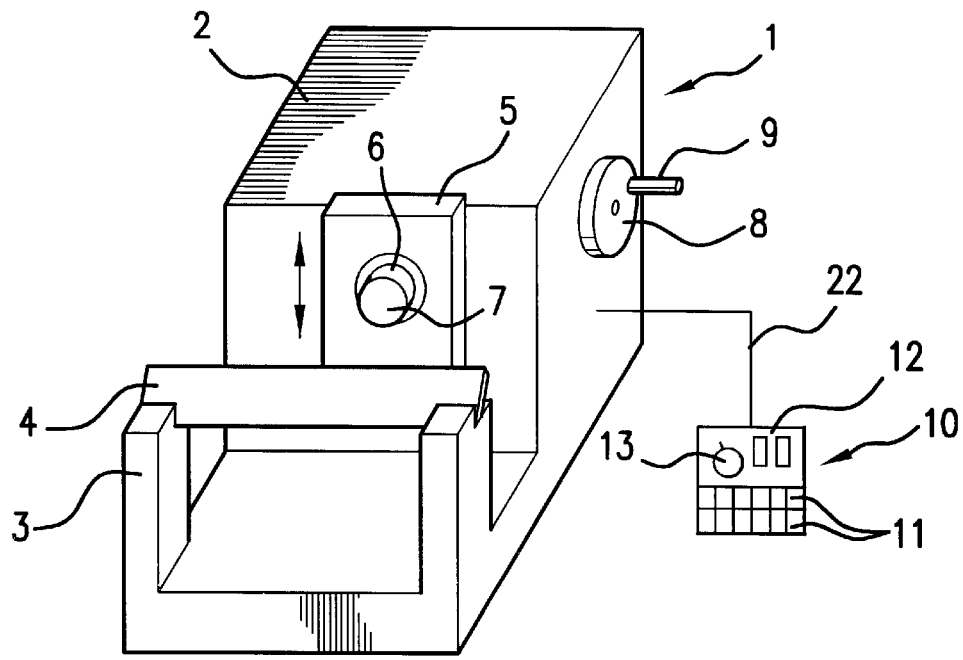
FIG. 1 is a perspective view of the microtome with a handwheel and an externally arranged control panel.

In the microtome of the invention a motorized drive system for generating the relative movement between the object and the cutting knife can be manually controlled by way of a conventional handwheel. For that purpose, the handwheel is not coupled to the motor via a mechanical drive train; instead, all that is provided is an encoder which converts the rotation of the handwheel into corresponding signals and forwards them to a control circuit. In the control circuit, the signals are analyzed, and the drive motor is activated accordingly. It is thus possible, with this configuration, to continue to operate the drive system in the accustomed sensitive fashion. This is especially advantageous in particular when, following a specimen change or knife change, the two need to be realigned with each other. By way of slight handwheel movements, the drive system can thus be moved sensitively forward and backward. In addition, by means of the control circuit, a reliable locking of the drive system can be effected whenever no signals are being supplied from the encoder. In this standby mode, the operator performs actions on the microtome, and there is a considerable risk of injury on the cutting knife. This risk of injury is minimized by automatic locking of the drive system.

In this context, the drive motor can be configured as a stepper motor, and locking of the drive can be accomplished by continuous energization of the stepper motor via the control circuit. A simply designed DC drive motor can, of course, also be provided. To lock the drive in this case, the control circuit either operates the motor in short-circuit mode or applies a holding current to it.

In a further embodiment of the invention, provision is made for arranging in the drive system an electromagnetic brake that is switchable via the control circuit. This brake essentially responds when the drive is switched to zero current or when no encoder signal is present. This brake can also be provided in addition to the functions already described for locking the drive system by way of the drive motor.

As an additional safety measure, it has proven advantageous for the output of the drive motor to be limited by way of the control circuit. For example, the motor output can be adjusted, as a function of the specimen that is to be sectioned, by way of a manual setpoint via a control panel. By means of this setpoint, the maximum current of the drive motor can then be limited to the necessary degree in the control circuit.

For comfortable handling of the handwheel, a mechanical counterweight can be associated therewith. The handwheel can moreover be equipped with a mechanical brake so that a rotating handwheel cannot continue to turn for a long period of time. For this purpose, provision is made for associating with the handwheel a mechanical brake having a spring pre-tensioned against the microtome. Other non-positive engagements can, of course, also be used.

Provision is also made for preselecting, by way of the control panel, a factor that modifies the ratio between the encoder signal and the motor rotation speed in the control circuit. The control panel can also, of course, have switches for the motorized drive system, so that once the cutting knife has been adjusted and aligned with the object, it is possible to switch over to the serial sectioning mode. In these cases the drive motor is no longer controlled by way of movements of the handwheel. As a safety measure, however, provision can also be made for the serial sectioning mode to be deactivated whenever the encoder once again delivers signals to the control device as a result of a handwheel movement.

In a further embodiment of the invention, the microtome drive system can additionally have an angle encoder, or the encoder can be configured as an incremental transducer with reference signal. The result of this is that the position of the cutting knife with respect to the object can be unequivocally identified. It is therefore also possible to vary the motor rotation speed and/or the motor output during a cutting cycle by way of the control circuit. It is advantageous, for example, if a high motor rotation speed and/or a low motor output is selected during motorized feeding of the object toward the cutting knife or vice versa, and if the motor rotation speed is reduced and/or the motor output increased during the actual sectioning operation.

In a further embodiment of the invention, the motor rotation speed and/or the motor output are reduced by the control circuit to a minimum if manual actions on the microtome become necessary, for example, as a result of an object change or knife change. This function can be implemented by the control device whenever, for example, a corresponding input is made via the control panel, or when a backward movement of the handwheel causes corresponding encoder signals to be received by the control device.

Figure 2:
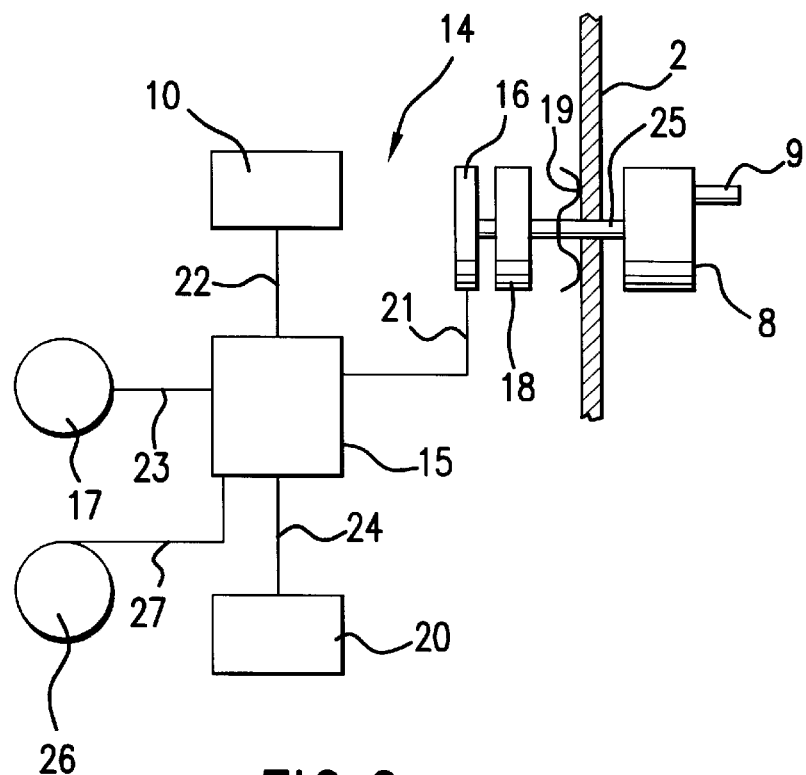
FIG. 2 is a schematic depiction of the drive system, with the handwheel and the control circuit.

The invention will be explained in more detail with reference to a preferred exemplary embodiment with the aid of the schematic drawings. FIG. 1 shows a microtome 1 having a microtome housing 2 and a knife holder 3 to receive a cutting knife 4. An object 7 is arranged on an object holder 6 that is mounted on a slide 5 so that it is movable in the direction of the double arrow. A rotatably mounted handwheel 8 having a handle 9 is arranged on microtome 1. Rotation of handwheel 8 causes object slide 5 to move and causes object 7 to be guided over the edge of knife 4. In contrast to conventional microtomes, handwheel 8 is not connected to object slide 5 by way of a mechanical drive train, but rather is connected to an encoder 16 arranged in the interior of microtome 1 (FIG. 2), and to a control circuit 15 downstream from the encoder (FIG. 2). The control circuit is connected via a control line 22 to an external control panel 10. Control panel 10 has a keypad 11 for numerical inputs, a rotary controller 13 for continuously variable inputs, and switches 12 for inputting specific switch positions and operating states.

FIG. 2 shows a schematic depiction of drive system 14 with handwheel 8 and control circuit 15. Handwheel 8 is arranged on a handwheel shaft 25 that passes through microtome housing 2 and carries at its other end encoder 16. Mounted on handwheel shaft 25 is a spring 19 that is tensioned against microtome housing 2. Spring 19, acting as a brake, is preferably provided so that the moving handwheel 8 comes to a stop after a certain period of time, and continued rotation of the handwheel is limited to a reasonable extent.

Handwheel shaft 25 also carries a counterweight 18. Counterweight 18 arranged on handwheel shaft 25 is preferably provided in order to ensure that handwheel 8 and encoder 16 run as uniformly as possible.

Rotating handwheel 8 causes encoder 16 to deliver corresponding signals via a control line 21 to control circuit 15. Control circuit 15 is connected via a control line 23 to a drive motor 17 in order to move object slide 5 (FIG. 1) via a gear train (not depicted). Drive motor 17 has current applied to it by the control circuit in accordance with the encoder signals. Control circuit 15 is configured so that, in standby mode, no encoder signals are received, and drive system 14 is locked by control circuit 15. For that purpose, drive motor 17 can, for example, be configured as a stepper motor and can be continuously energized. Alternatively, drive motor 17 is configured as a DC motor and is acted upon by a holding current or is operated in short-circuit.

Additionally or alternatively, provision can be made for an electromagnetic brake 26, connected via a control line 27 to control circuit 15, whereby it can be activated.

In a further embodiment of the invention, an angle coder 20 is connected to control circuit 15 via a control line 24. The position of the object with respect to the cutting knife can be ascertained by way of angle coder 20.

A variety of parameters can be input by way of control panel 10 connected to control circuit 15. For example, an output limitation and/or rotation speed limitation for the drive motor can be set. These limitations can also have different settings within a single cutting operation. For example, the actual cutting operation should be performed slowly and with a high level of force, whereas while the object is being fed again toward the cutting knife, the output of the drive motor is limited and the rotation speed is increased.

In addition, by way of switch 12 on control panel 10, microtome 1 can be switched into an operating mode of continuous serial sectioning, regardless of any actuation of handwheel 8.

The invention is not limited to a rotary microtome, but can of course also be used in a disk microtome or a sliding microtome.

The disclosure of German Patent Application No. 199 11 163.4, filed Mar. 12, 1999, is incorporated by reference in its entirety.

It will be readily apparent that many other embodiments of the present invention can be constructed in accordance with the teachings contained herein. It is intended that all such embodiments be encompassed by the appended claims.

We claim:

1. A microtome for producing thin sections from an object, comprising: a housing; a cutting blade mounted in association with the housing; an object holder movably mounted with respect to the housing to hold the object to be sectioned; and a drive system contained within the housing for producing relative cutting movement between the cutting blade and the object holder, the drive system including an automatic drive system having a drive motor and a control circuit for controlling operation of the drive motor and a manual drive system for manually initiating relative cutting movement between the cutting blade and the object holder, the manual drive system including a handwheel and an encoder, wherein the handwheel is connected to the encoder and the encoder is connected to the control circuit for delivering corresponding signals to the control circuit upon rotation of the handwheel, and the control circuit is configured to activate the drive motor in accordance with the signals from the encoder and to control at least one electromechanical device to prevent relative cutting movement between the cutting blade and the object holder in a standby mode defined by an absence of signals from the encoder.

2. The microtome as defined in claim 1, wherein the at least one electromechanical device comprises said drive motor and said drive motor comprises a stepper motor and wherein, in the standby mode, the control system is configured to supply current to the stepper motor to lock the drive system.

3. The microtome as defined in claim 1, wherein the at least one electromechanical device comprises said drive motor and said drive motor comprises a DC motor, and wherein, in the standby mode, the control circuit is configured to lock the drive system.

4. The microtome as defined in claim 1, wherein the control circuit is configured to limit the output of the drive motor.

5. The microtome as defined in claim 4, wherein the output of the drive motor is limited by an adjustable maximum current, as a function of the material of the object that is to be cut.

6. The microtome as defined in claim 1, wherein the at least one electromechanical device comprises an electromagnetic brake that is switchable by way of the control circuit and wherein, in the standby mode, the control system engages the electromagnetic brake to prevent relative cutting movement between the cutting blade and the object holder.

7. The microtome as defined in claim 1, further comprising at least one counterweight associated with the handwheel.

8. The microtome as defined in claim 1, further comprising a mechanical brake with a nonpositive engagement in the drive system.

9. The microtome as defined in claim 8, wherein the nonpositive engagement comprises a spring pre-tensioned against the microtome housing.

10. The microtome as defined in claim 1, wherein the control circuit is configured to adjust the ratio of the encoder signals to the motor rotation speed.

11. The microtome as defined in claim 1, wherein the drive system further comprises an angle coder or the encoder is configured as an incremental transducer, whereby the position of the cutting knife with respect to the object is identifiable by the control circuit.

12. The microtome as defined in claim 11, wherein the control circuit is configured to vary the motor rotation speed and/or the motor output during a cutting cycle.

13. The microtome as defined in claim 12, wherein the control circuit is configured to raise the motor rotation speed during the cutting operation and to raise it again after the cutting operation.

14. The microtome as defined in claim 13, wherein the control circuit is configured to raise the motor output during the cutting operation and to limit it after the cutting operation.

15. The microtome as defined in claim 1, further comprising a control panel connected to the control circuit, the control panel having a control member for manually inputting at least one modifiable parameter for controlling the microtome.

16. The microtome as defined in claim 15, wherein the control panel has a switch for serial cutting, and the drive motor is activated directly via that switch and the control circuit.

17. The microtome as defined in claim 1, wherein the control circuit is configured to set to a minimum the output and the rotation speed of the drive motor.

18. The microtome as defined in claim 1, wherein the microtome comprises a disk microtome, a rotary microtome, a sliding microtome or a vibratome.

19. The microtome as defined in claim 1, wherein the handwheel is rotatable in a forward and in a reverse direction, the encoder delivers signals corresponding to the direction of rotation of the handwheel, and the control circuit activates the drive motor in forward and reverse directions corresponding to the signals corresponding to the direction of rotation of the handwheel.

20. The microtome as defined in claim 1, wherein the encoder delivers to the control circuit electrical signals corresponding to the extent to which the handwheel is rotated, for activating the drive motor in the drive system.

21. A microtome for producing thin sections from an object, comprising: a housing; a cutting blade mounted in association with the housing; an object holder movably mounted with respect to the housing to hold the object to be sectioned; a drive system contained within the housing for producing relative cutting movement between the cutting blade and the object holder, the drive system including an automatic drive system having a drive motor and a control circuit for controlling operation of the drive motor and a manual drive system contained within the housing for manually initiating relative cutting movement between the cutting blade and the object holder, the manual drive system including a handwheel and an encoder, wherein the handwheel is connected to the encoder and the encoder is connected to the control circuit means for delivering corresponding signals to the control circuit upon rotation of the handwheel, wherein the control circuit is configured to activate the drive motor in accordance with the signals from the encoder; and means, including the control circuit, for preventing relative cutting movement between the cutting blade and the object holder in a standby mode, wherein the standby mode is defined by an absence of signals from the encoder.

22. The microtome as defined in claim 21, wherein the drive motor comprises a stepper motor, and wherein the locking means comprises the control system configured to supply current to the stepper motor to lock the drive system.

23. The microtome as defined in claim 21, wherein the drive motor comprises a DC motor, and wherein the locking means comprises the control circuit configured to operate the DC motor to lock the drive system.

24. The microtome as defined in claim 21, further comprising an electromagnetic brake that is switchable by way of the control circuit, and wherein the locking means comprises the control system configured to engage the electromagnetic brake in the standby mode to prevent relative cutting movement between the cutting blade and the object holder.

* * * * *